United States Patent [19]

Freedland

[11] 4,409,974
[45] Oct. 18, 1983

[54] BONE-FIXATING SURGICAL IMPLANT DEVICE

[76] Inventor: Jeffrey A. Freedland, 693 Montgomery St., Brooklyn, N.Y. 11213

[21] Appl. No.: 278,084

[22] Filed: Jun. 29, 1981

[51] Int. Cl.³ .............................................. A61F 5/04
[52] U.S. Cl. ............................ 128/92 B; 128/92 BC; 128/92 CA
[58] Field of Search ........... 128/92 BA, 92 CA, 92 R, 128/92 BC, 92 B; 294/97

[56] References Cited

U.S. PATENT DOCUMENTS

| | | | |
|---|---|---|---|
| 2,077,804 | 4/1937 | Morrison | 128/92 BA |
| 2,685,877 | 8/1954 | Dobelle | 128/92 CA |
| 4,091,806 | 5/1978 | Aginsky | 128/92 BC |
| 4,236,512 | 12/1980 | Aginsky | 128/92 BA |
| 4,237,875 | 12/1980 | Termanini | 128/92 BA |
| 4,275,717 | 6/1981 | Bolesky | 128/92 BC |

*Primary Examiner*—Kyle L. Howell
*Assistant Examiner*—C. W. Shedd
*Attorney, Agent, or Firm*—Kirschstein, Kirschstein, Ottinger & Cobrin

[57] ABSTRACT

A surgical implant for the fixation of bone portions and methods for using the same to reduce bone fractures with or without the use of bone fixating plates and in a variety of surgical procedures where rigid fixation of bones or bone portions even under great stress is required. The implant has a generally frusto-conical head with a plurality of arms hingeably connected thereto, the arms capable of moving from a retracted position to and extended position. A rectilinear bore having a diameter slightly greater than the greatest effective transverse dimension of the implant device with the arms in the retracted position is drilled through the bone portions to be fixated. A guiding tube or shaft is provided to guide the head of the implant device with the connected arms in retracted position into the bore. After the head and arms have been inserted until the device spans the interspace between the bone portions to be fixated, a deployment arrangement is actuated to cause the arms to move from the retracted position to an extended position wherein the head and arms no longer fit through the hole and the implant device is anchored in the bone portions. The end of the implant device that protrudes from the hole is attached to a securing apparatus which applies compressive force to the outermost bone portions and creates tension in the implant device. A collapsing unit is provided so that, if removal of the implant is desired, the securing apparatus can be detached from the bone portions, the arms can be returned from the extended position to the retracted position and the implant can be removed from the bore.

18 Claims, 17 Drawing Figures

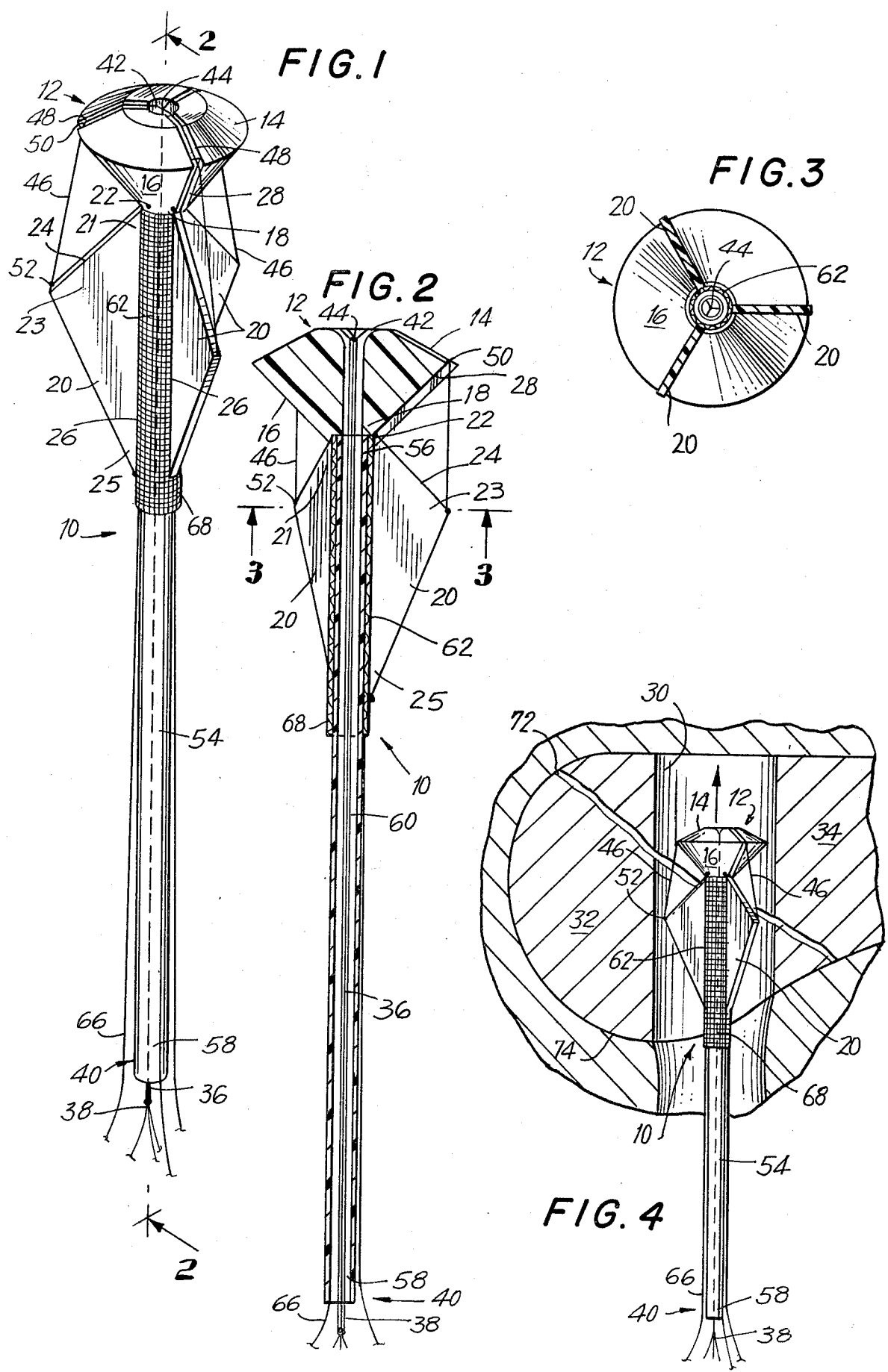

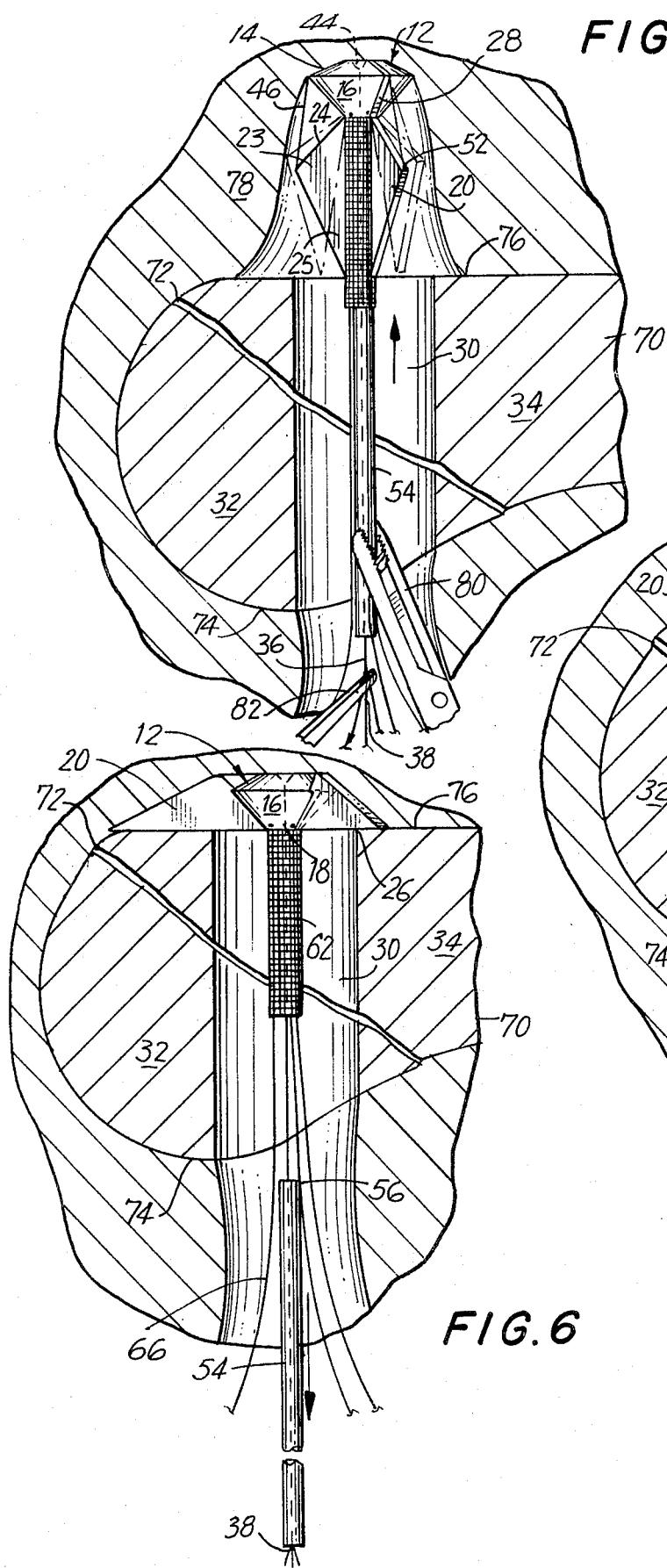
FIG. 5
FIG. 6
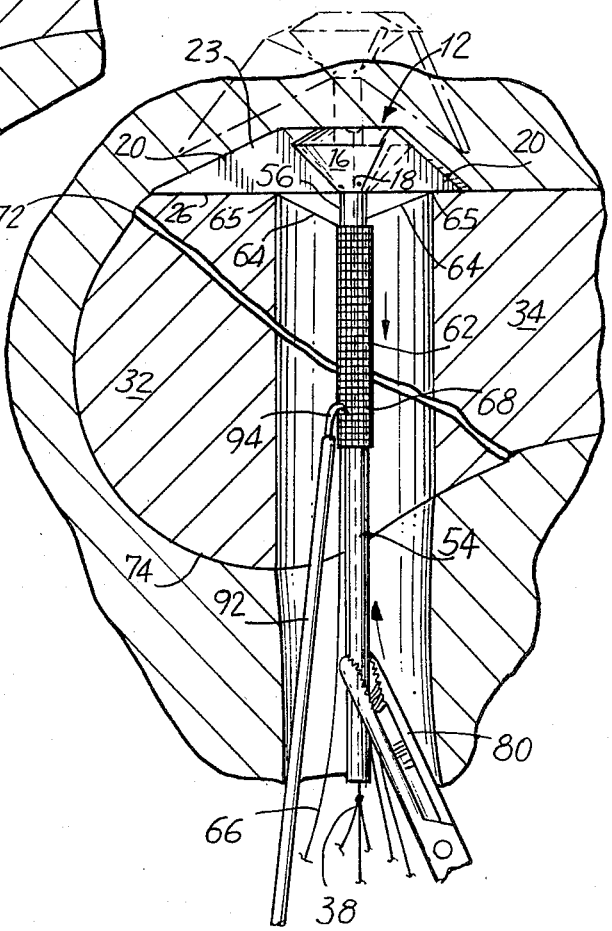
FIG. 7

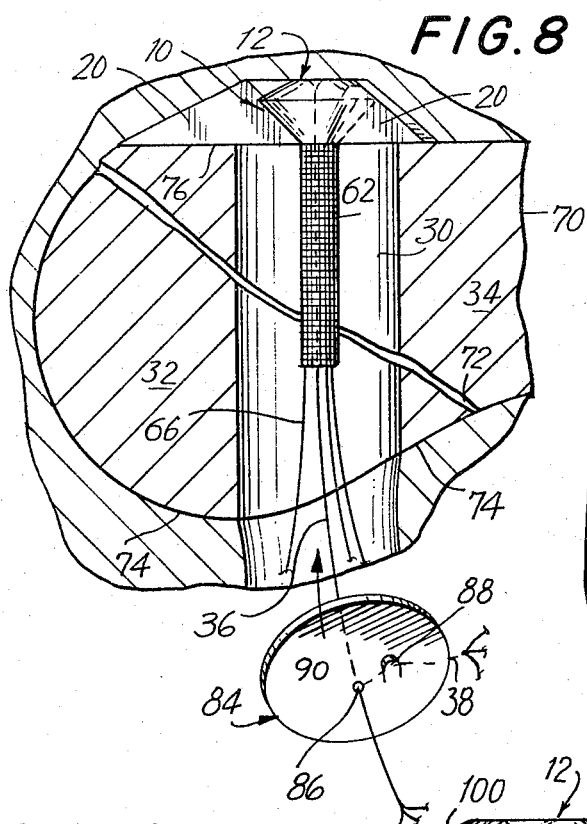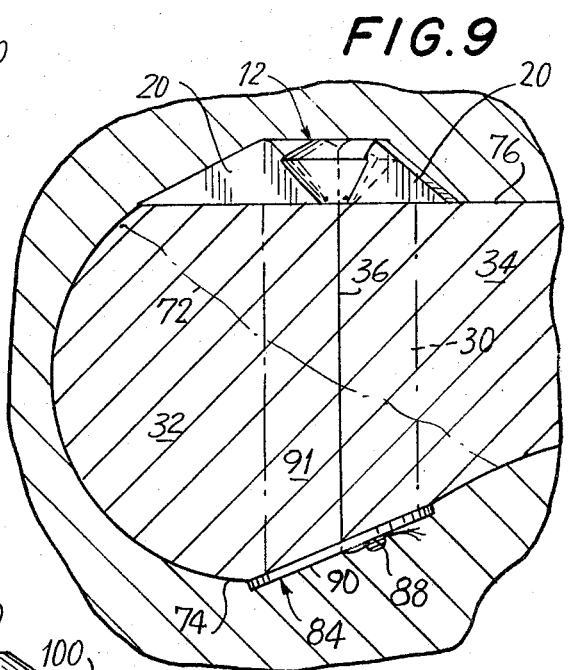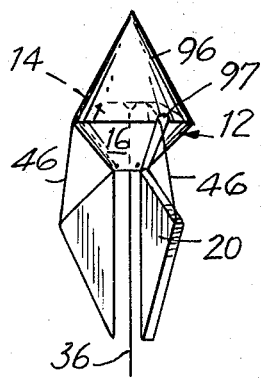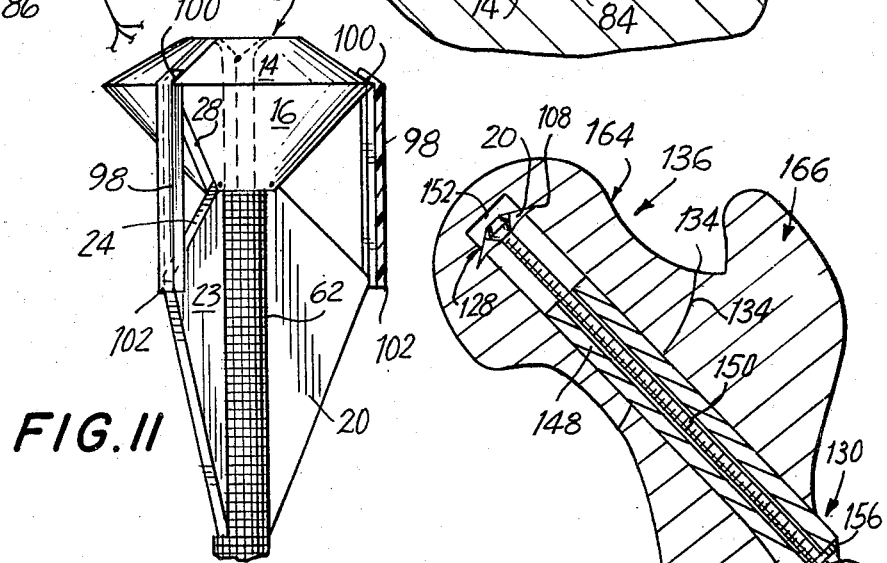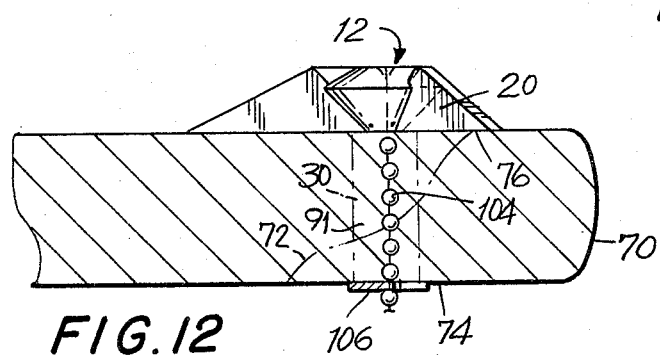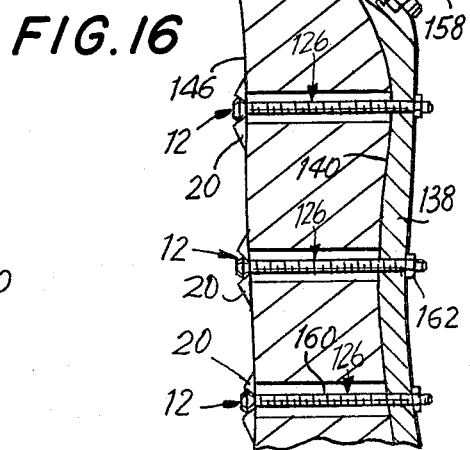

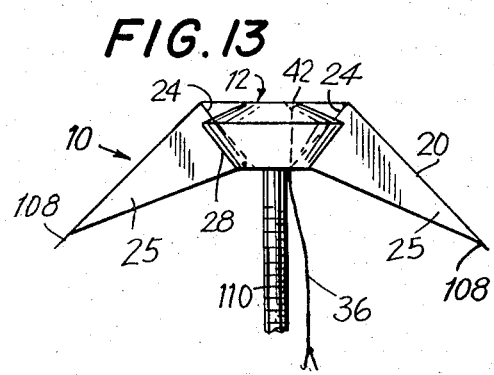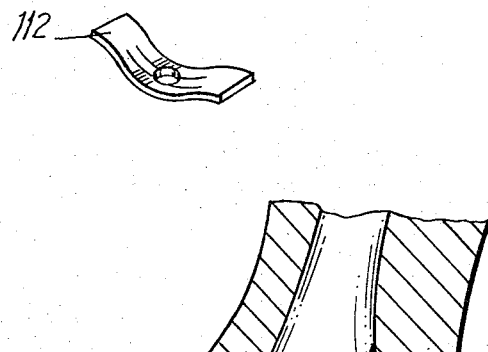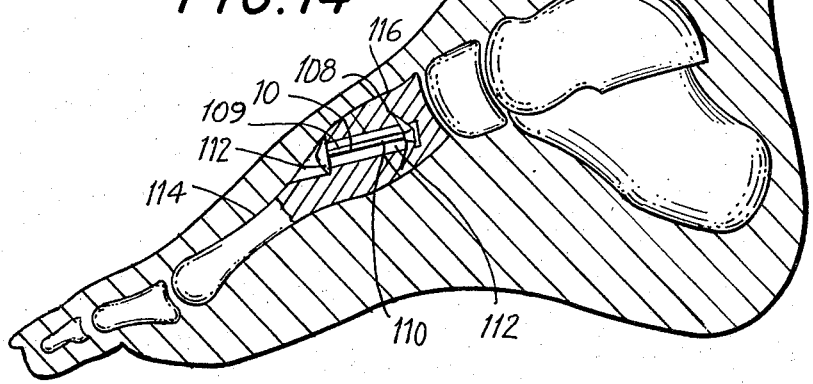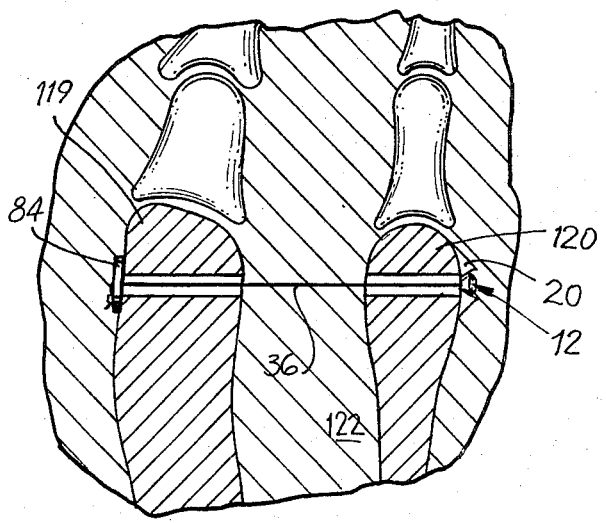

BONE-FIXATING SURGICAL IMPLANT DEVICE

BACKGROUND OF THE INVENTION

1. Field of the Invention

The present invention relates generally to surgical implant devices and, more particularly, to implant devices utilized in procedures where rigid internal fixation of bone portions is desired.

2. Description of the Prior Art

Various devices and methods have been used in the prior art for the fixation of bones or bone portions. In the case of procedures wherein the fixation of delicate bones is required, fine metallic wires are secured through holes drilled in the bones. Wires and pins of somewhat greater diameter can also be inserted through the bones with an apparatus such as a wire driver which resembles a rotary power drill. Staples have been employed as well to fixate osteotomy sites. In the case of larger bones, particularly in the reduction of fractures, self-tapping bone screws are often inserted into drill holes to secure portions of the bone on either side of the fracture and enable healing to occur.

Where greater stabilization is required or where in the case of a fracture, for example, a substantial amount of stress will be placed on the fragmented bone portions because of the position of the fracture, the weight of the patient, the nature of athletic or other activity in which the patient wishes to engage, or similar factors, bone-fixating compression plates are often placed across the fracture line and are anchored by screws inserted through the plates and into the bone on either side of the fracture.

In the open reduction and internal fixation of a variety of fractures of the proximal femur and femoral neck, combination screw and plate devices have been utilized wherein a cavity in the femoral neck is reamed out and a plate is put against the outer surface of bone through which a large screw or bolt is inserted and screwed into the reamed-out cavity. The screw or bolt is attached to a plate which abuts against the cortex of the femur. The plate is anchored in the bone by smaller bone screws.

The use of prior art devices such as screws or screw and plate combinations where compression of bone portions, for example in the case of fractures, is required, has significant drawbacks. Bone screws are normally inserted through the cortex of a bone and secured in the relatively soft bony material in the medulla, and the primary compressing force is provided by threads of the screw gripping into the medulla and the head of the screw pressing against the cortex. Particularly in the case of osteoporotic bone, the bone screws frequently do not provide sufficient compression on the bone to reduce the fracture properly.

In addition, when bone screws are used, even in cases where the opposite cortex is purchased, a very large hole is created through the cortex and medullary bone which cannot be filled in with bony material while the screw is in position. If the screw is removed, the areas of the bone immediately surrounding the screw hole have a greater susceptibility to cracking or fracturing than normal bone, and the bone is not filled in by natural healing processes for a considerable amount of time.

There are a number of prior art devices specifically designed for reducing fractures of the femoral neck and for fixating the portions of the femur which lie on either side of the fracture. Aside from the screw and plate devices which have been mentioned previously, there are various bolt-like devices which can be inserted into the femoral neck through a drill bore, either alone or inside the tube of a compression plate and tube apparatus.

In certain of these devices, a central shaft is encased in a tube which is split at the end which will be inserted into the femur and, as the central shaft is screwed into the femur, the split ends of the tube diverge and grip into the medullary material surrounding the drill bore. These devices are complex to manufacture and do not provide a great deal of compressive force necessary to reduce the fracture, impact the bone fragments and immobilize the bone fragments with respect to each other.

Another prior art device used with femoral fractures comprises a central threaded shaft encased in a tube. At the top of the tube, the end which will be inserted into the femoral neck, there are vertical slots, and inside the tube adjacent to the slots are articulated blade-like members. When the central shaft is screwed into the tube towards the top end thereof, the blade-like members are pushed outward through the slots and lock into place. This device is also complex to manufacture and has a number of drawbacks in surgical applications. In order to ensure that no large portion of the device protrudes from the bore after the device has been inserted and the blades have been opened, the bit used to drill the bore is left in the bore while the femoral shaft is manually hammered towads the femoral head, such as with a mallet, until the operator feels that the fracture has been closed and the bone portions have been impacted. The length of the bore is then determined by reference to the length of drill bit that is inside the bone, a device with a length slighly greater than the length of the bore is then inserted and the blades are opened when the device is in place.

This procedure of impacting the bone fragments by hammering the femoral shaft towards the femoral head is dangerous; the blows of the mallet will frequently drive bone chips, which may surround the femoral head in the case of a fractured femoral neck, into the hip joint or other surrounding tissue. Moreover, the devices of numerous difficult lengths must be available so that a device can be chosen with a suitable length, corresponding to the length of the bore, so that no significant portion will protrude from the bore after the device is inserted.

None of the prior art devices utilized to reduce fractures generally, or femoral fractures specifically, can be constructed simply and yet provide a great deal of compression on a bone to reduce fractures and/or fixate bone portions. In addition, none of the prior art devices which can be utilized where a great deal of tensile strength is required are of such construction that any protruding portion of the device can be simply cut or clipped off and discarded, which would obviate the necessity for manufacturing devices of a wide variety of lengths and having a number of such devices available during surgery so that one of suitable length can be selected.

SUMMARY OF THE INVENTION

Objects of the Invention

It is an object of the present invention to provide a surgical implant device for the fixation of bone portions which overcomes the aforementioned drawbacks of the prior art.

Another object of the present invention is to provide an implant device for the fixation of bone fragments that applies a substantial amount of compression on the bone fragments and maintains them rigidly in position.

A further object of the present invention is to provide an implant device which can be inserted into a relatively narrow bore which is cleanly drilled through the bone portions to be fixated.

An additional object of the present invention is to provide an implant device which can be easily removed and repositioned even several days after it has been inserted and secured.

Still another object of the present invention is to provide an implant device wherein only a narrow thread, wire or pin is passed through the bore drilled through medullary bone and thus filling in of the initial drill bore with bony material can proceed rapidly even while the implant is in position.

Still a further object of the present invention is to provide a bone-fixating implant which can be initially inserted and removed utilizing surgical tools which are standard to the operating room major surgical pack.

Yet another object of the present invention is to provide an implant device which can be adapted for use in a wide variety of orthopedic procedures where fixation of bones is required.

Yet a further object of the present invention is to provide a surgical implant device that can be utilized in combination with prior art apparatus such as bone-fixating compression plates and angled blade plates in procedures where resistance to a great amount of stress is required.

Yet another object of the present invention is to provide an implant device which can provide sufficient compression to reduce fractures whether or not a bone cortex is available upon which the head and arms of the implant device can be anchored.

An additional object of the present invention is to provide an implant device whose length can be adjusted after insertion by cutting off any excessive protruding portions.

Features of the Invention

In keeping with these objects and others which will become apparent hereinafter, one feature of the invention resides, briefly stated, in a surgical implant device for fixating bones in which a round rectilinear bore has been drilled, comprising a head positioned at one end region of the device with a plurality of arms hingeably connected thereto. The arms are capable of movement from a retracted position, wherein the greatest effective transverse dimension of the head and of the connected arms is less than the diameter of the hole drilled through the bone so that the head with the arms in the retracted position may be inserted into the bore, to an extended position wherein the greatest effective transverse dimension of the head and connected arms is greater than the diameter of the bore.

In accordance with the invention, the head and arms of the device are inserted into the bore drilled in the bone until the device spans the division or interspace between the bone portions to be fixated and the head and arms are positioned in, above or against a terminal bone portion, while the lower end region of the device, which is opposite the head, still protrudes from the hole. Actuating means is provided for deploying the arms by radial upward swinging movement from the retracted position to the extended position after the head and arms have reached the desired position in relation to the bone portions, the deployment of the arms effectively preventing the arms and head from being removed retrogradedly from the bore. After the deployment of the arms, the lower end of the device, the end which protrudes from the bore, is pulled away from the bore until the arms and head are firmly anchored in or against the terminal bone portion. A means is provided for firmly securing the protruding end region of the implant device against the portions of the bone cortex surrounding the bore. Any excessive protruding portion of the implant device can be cut or clipped off after the device is secured.

Compression of the bone portions fixated by use of the implant device of the present invention is provided by the clamping force of the head and arms drawing the terminal bone portion toward the secured end of the device and the securing means which tightly fastens the opposite end of the implant device to the bone cortex portions surrounding the bore.

In accordance with another feature of the invention, a guiding means is provided for the insertion of the head and arms of the implant device into the bore until they reach the desired position in the terminal bone portion.

Once the head and arms have reached the desired position in the terminal bone portion, and the arms have been extended, the guiding means is detached from the implant device and removed from the bore. In addition, a means for collapsing the arms from the extended position to the retracted position after the insertion of the head and arms into the bore is provided to permit the removal of the head and arms from the bore when, for example, repositioning of the device is desired.

The removal of the implant device of the present invention from the bore in the bone portions after the device has been secured is accomplished by detaching the securing means from the end region of the device and then inserting the guiding means into the bore and inside the collapsing means until it is adjacent to the head in or on the terminal bone portion. A surgical hook or similar device is inserted into the hole until it grasps the collapsing means. The collapsing means is pulled towards the end region of the device while the guiding means is simultaneously pushed through the bore against the head and arms to move them from the position in which they were anchored in or against the terminal bone portion to a position wherein the arms are freed for radially inward swinging movement. The arms are then collapsed from the extended position to the retracted position. After the collapsing of the arms, the entire device is removed from the bore by pulling on the lower end region of the device.

Repositioning of the implant device after its removal is accomplished according to the present invention by modifying the initial bore or by drilling a second bore in a desired site and inserting the device in accordance with the procedure previously described.

In accordance with yet another feature of the present invention, the actuating means for deploying the arms comprises a multi-filament thread having a free end near the lower region of the device. An elongated aperture is provided which extends through the head substantially in the direction of the lower end region. The thread extends from the aperture in the head and has a splayed end at which the thread is divided into a plurality of individual filaments, the number of said filaments being equal to the number of arms attached to the head. Each of the individual filaments which extends from the splayed end of the thread is operatively attached to a portion of a different one of the arms spaced away from the head. When tension is caused in the thread, for example, by pulling on the free end thereof, the filaments which are attached to the arms caused the deployment of the arms from their retracted position to their extended position.

The guiding means of the present invention can comprise an elongated hollow tubular member having an upper end adjacent and coupled to the head and a lower end adjacent to the opposite end region of the implant device. The tubular member has a central interior passageway through which the multi-filament thread is threaded, entering the tubular member at its upper end adjacent to the head and emerging from the tubular member at its lower end with the free end of the thread extending beyond the lower end of the tubular member.

The collapsing means of the present invention can comprise a cylindrical mesh which girdles a portion of the tubular guiding member and is slideably mounted thereon. When the device is inserted into the bore, the collapsing mesh is positioned at the upper end of the tubular member proximate to the lower region of the head. A plurality of collapsing filaments, the number of which is equal to the number of arms and each of which originates in the cylindrical collapsing mesh, each has an outer end attached to a portion of a different one of the arms. When collapsing of the arms from the extended position to the retracted position is desired, the cylindrical collapsing mesh is grasped and pulled in a direction away from the head towards the lower end of the tubular member, causing the collapsing filaments to pull the arms downward and causing the arms to collapse.

The collapsing mesh is composed of a body-dissolvable suture-type material so that it can substantially completely dissolve or disintegrate in vivo after a period of time.

When the implant device of the present invention is in position and secured with the head and arms in or against the terminal bone portion and the lower region secured to the bone portions surrounding the bore, the only portion of the device which remains in the bore between the head and the securing means is the multi-filament thread, in one embodiment of the invention.

In another embodiment of the invention, useful where greater tensile strength in the implant device is required, a wire, pin, or shaft is attached to the head and extends towards the lower end region of the implant. The aperture in the head is adjacent to the area of juxtaposition between the wire or pin and the head and the multi-filament thread extends through the aperture and runs along the side of the wire, pin or shaft with its free end adjacent to the lower end of the pin or wire.

Where a wire, pin or shaft is used, the securing means is fastened thereto instead of to the multi-filament thread.

Whether a wire, pin or shaft is utilized or the multi-filament thread alone joins the head to the securing means, the portion of the implant which is inside the bore is of very small diameter, unlike the screws utilized for compression in the prior art, and bony material can begin to fill in the bore around the thread, wire, pin or shaft almost immediately, thus promoting healing and strengthening the bone.

The securing means employed in accordance with the present invention can constitute, in the case where only the multi-filament thread and no pin, wire or shaft is attached to the head, a disk or button with a hole in the center thereof through which the free end of the thread is inserted and with a prong extending from the bottom thereof around which the thread may be secured. A similar arrangement can be utilized where flexible thin wires are attached to the head in addition to the multi-filament thread.

In those embodiments where a pin or shaft is attached to the head, the pin or shaft is threaded or has a series of annular flanges, at least on its lower end, and a bolt-fastening arrangement such as a washer and nut or a push-on nut can be secured to the lower end of the pin or shaft that protrudes from the hole to secure the implant device in position. Even where a pin or shaft is utilized, the pin or shaft is sufficiently thin and flexible so that excessive length thereof can be clipped off.

The novel features which are considered as characteristic of the invention are set forth in particular in the appended claims. The invention itself, however, both as to its construction and its method of operation, together with additional objectives and advantages thereof, will be best understood from the following descriptions of specific embodiments when read in connection with the accompanying drawings.

BRIEF DESCRIPTION OF THE DRAWINGS

FIG. 1 is a perspective view of one form of a surgical implant device in accordance with the present invention.

FIG. 2 is an axial sectional view taken substantially along line 2—2 of FIG. 1.

FIG. 3 is a transverse sectional view taken substantially along line 3—3 of FIG. 2.

FIG. 4 shows a schematic sectional view of a fractured bone with a round rectilinear bore drilled through the bone portions on either side of the fracture and an elevational view of the implant device as it is being inserted through the bore in the bone portions.

FIG. 5 shows the same view of the bone as FIG. 4 but with the implant device inserted beyond the terminal bone portion, and illustrates in phantom lines the beginning of deployment of the arms from the retracted position to the extended position, effected by means of a tweezers or forceps grasping the multi-filament thread and pulling the same away from the head while the tubular guiding member is held and pushed towards the head with a pair of surgical pliers.

FIG. 6 shows a schematic sectional view of the fractured bone as in the previous figures and an elevational view of the implant device with arms in extended position and pressing against the cortex of the terminal bone portion, with the tubular guiding member being detached from the implant and removed from the hole.

FIG. 7 shows a schematic sectional view of the fractured bone with an elevational view of the implant device during the process of removal thereof, the head and arms shown in phantom lines being lifted away from the cortex of the terminal bone portion and a tissue hook inserted into the hole pulling down on the collapsing mesh while the tubular guiding member is pushed upward so that the arms will be collapsed from the extended position to the retracted position.

FIG. 8 shows a schematic sectional view of a fractured bone, an elevational view of the implant device with the arms in extended position compressed against the cortex of the terminal bone portion and a perspective view of a securing disk with a prong extending therefrom, with the free end of the multi-filament thread shown in phantom being tied to the prong.

FIG. 9 shows a schematic sectional view of the fractured bone and an elevational view of the implant device secured in position with the cylindrical collapsing mesh having dissolved and bone healing in process both at the fracture site and in the hole around the multi-filament thread.

FIG. 10 is a partial elevational view of the head and arms of a modified form of implant device with a pointed boring cap mounted on the upper surface of the head.

FIG. 11 is a partial elevational view of the upper portion of another modified form of implant device having elongated shielding strips dependent from the upper surface of the head and covering the grooves in the lateral surface of the head as well as the outer edges of the arms.

FIG. 12 is a schematic sectional view of a fractured bone and an elevational view of a further modified form of implant device secured in position with a series of balls spaced along the length of the multi-filament thread and with the fastening means being a button with a radial slot therein, said slot having a portion of the multi-filament thread which lies between two of the balls fitted therein.

FIG. 13 is a partial elevational view of yet another modified form of implant device having arms terminating in a sharp edge and having a threaded shaft attached to the head.

FIG. 13A is a perspective view of a bowed push-on nut that can be used to secure an implant device having a shaft with a plurality of annular flanges thereon.

FIG. 14 is a schematic view of the human foot showing an implant device with arms terminating in a sharp edge in position between the base of the first metatarsal bone and the distal surface of the medial cuneiform bone, with the sharp terminal edges of the arms anchored in the medullary material inside the cuneiform, the base of the first metatarsal having been resected and the articular cartilage of the cuneiform having been also removed in order to allow bone-to-bone fusion at the site.

FIG. 15 shows a sectional view of the first and second metatarsal bones of a human foot with an implant device secured in position having its arms extended and pressing against the lateral cortex of the second metatarsal and the securing disk pressing against the medial cortex of the first metatarsal, thus urging the first metatarsal toward the second metatarsal and reducing the angle therebetween.

FIG. 16 is a schematic view of a human femur with a fractured neck and an elevational view of a plurality of implant devices in fully deployed and secured condition attaching a compression plate apparatus to the femur to fixate and stabilize the bone portions on either side of the fracture.

DESCRIPTION OF THE PREFERRED EMBODIMENTS

As shown in the accompanying drawings, and particularly in FIG. 1 thereof, the surgical implant device of the present invention, denoted generally by the numeral 10, has a substantially frusto-conically shaped head 12 which comprises an upper surface 14, a lateral surface 16 and a lower end 18. The illustrated configuration of the head is not central to the practice of the invention although it is preferred. A plurality of arms 20, i.e., two or more, each having a proximal end 21 adjacent to the head 12, an offset portion 23, and a distal end 25, are attached to the lower end 18 of the head 12 by hinges 22 which independently of one another link the proximal end 21 of each of the arms to the lower end 18 of the head 12 with equi-angular spacing therebetween. Each of the arms 20 has an upper edge 24 and an inner edge 26. Although the illustrated shape of the arms is preferred, other shapes may be utilized. For example, the arms may be straight and of uniform cross-section along their lengths rather than having the intermediate outwardly extending hump illustrated.

As further shown in FIG. 1, shallow, elongated grooves 28 are provided in the lateral surface of the head 12, said grooves extending from the upper surface 14 of the head 12 to the lower end 18 thereof. The number of grooves 28 is equal to the number of arms, and the grooves are shaped, dimensioned and positioned to freely receive the upper edges 24 of the arms 20 when the arms are pivotally swung upwardly about the hinges 22 as shown in FIG. 5 and FIG. 6.

In accordance with the present invention, an actuating means is provided to deploy the arms 20 by rotational movement about the hinges 22 from the collapsed position wherein each of the upper edges 24 of the arms 20 is at a predetermined distance from the lateral surface 16 of the head 12 and the distal ends 25 are close to the longitudinal axis of the device to an extended position wherein the upper edges 24 of the arms 20 are substantially adjacent to the lateral surface 16 of the head 12 and are seated in the grooves 28, and the distal ends 25 are remote from said axis.

In operation, the head 12 and the attached arms 20 will be inserted into the elongated round rectilinear bore 30, as shown, for example, in FIG. 4, which will be drilled across the fracture and through the bone portions 32 and 34 which are to be fixated.

As shown in FIGS. 1 and 2, the actuating means for deploying the arms 20 comprises an elongated multi-filament thread or thread bundle 36 having a free end 38 near the lower end region 40 of the device which is at the opposite end of the device 10 separate from the head 12. The multi-filament thread 36 extends from its lower end 38 near the lower end region 40 of the device upward towards the head 12 at the opposite end region of the device. The head 12 has an elongated rectilinear central longitudinal aperture 42 which extends from the upper surface 14 of the head to the lower region 18 of the head 12. The multi-filament thread 36 extends through the aperture 42 and has a splayed end 44, which splayed end is located within the aperture 42 proximate to its opening at the upper surface 14 of the head 12, and at which splayed end 44 the thread 36 divides into a plurality of individual filaments 46. Each of the individual filaments 46 extends along the upper surface 14 of the head 12 and is positioned in a guide channel 48 which runs from the upper end of the aperture 42 to a point where one of the grooves 28 meets the upper surface of the head 12. Each of the multi-filament threads 36 then extends downwardly over the upper end 50 of a groove 28 to a thread end 52 attached to an intermediate point of the associated arm, preferably to offset portion 23.

As further illustrated in FIGS. 1 and 2, a guiding means for directing the insertion of the implant device 20 into the bore 30 drilled through the bone portions 32, 34 which are to be fixated is provided in accordance with the present invention, said guiding means comprising in the preferred embodiment an elongated hollow straight tubular member 54 having an upper end 56 adjacent to the lower end 18 of the head 12, a lower end 58 adjacent to the lower end region 40 of the device 10, and an interior passageway 60 which runs the full length of the tubular member 54. The tubular member 54 is detachably affixed at its upper end 56 to the lower end 18 of the head 12 by a non-permanent adhesive or interlocking edges.

The tubular member 54 and its interior passageway 60, shown in FIGS. 1 and 2, have a common longitudinal axis which is substantially colinear with the longitudinal axis of the aperture 42 of the head 12. The multi-filament thread 36 is threaded through the interior passageway 60 of the tubular member 54 until the free end 38 of the thread 36 extends beyond the lower end 58 of the tubular member 54 and the thread 36 is thereby enshrouded by the tubular member 54 from the point where the thread emerges from the upper end of the aperture 42 in the head 12 to a point proximate to its free end 38.

In accordance with the preferred embodiment of the present invention, a collapsing means is provided which is operative for collapsing the arms 20 from their radially extended (deployed) position to their collapsed position. As shown in FIGS. 1 and 2, said collapsing means comprises a tubular mesh 62 which is slideably mounted on the tubular member 54 and which, prior to the actuation of the collapsing means, is positioned adjacent to the lower end 18 of the head 12 and girdles the upper portion of the tubular member 54. A plurality of equiangularly spaced collapsing filaments 64, which are best illustrated in FIG. 7, extend from the upper end of the cylindrical mesh 62, the number of said collapsing filaments being equal to the number of arms 20, and each of said collapsing filaments having an outer end 65 attached to an intermediate point of the inner edge 26 of a different one of the arms. The collapsing filaments 64 can be extensions of filaments that are integrally woven into the mesh 62 or they can be separate filaments which are adhered, sewn or otherwise fastened to the mesh 62.

The collapsing means further comprises a plurality of pulling filaments 66, illustrated, inter alia, in FIGS. 1 and 7, which extend from the lower end 68 of the cylindrical mesh 62 downwardly toward the lower end region 40 of the device 10. Like the collapsing filaments 64, the pulling filaments 66 may be extensions of filaments or threads integrally woven into the mesh or may be individual filaments attached or adhered to the mesh 62.

The implant device 10 of the present invention is adaptable for use in a variety of surgical procedures where rigid fixation of bones or bone portions is required, even where said bone portions will be under a great deal of stress tending to displace them from the fixated positions. Particular examples of where the implant device 10 is especially useful and greatly superior to the prior art devices currently used for the same purpose are in the reduction of fractures, both traumatic and surgically induced, in the temporary immobilization of bones to permit healing after resection of a portion thereof, and in corrective surgery where the fusion of adjacent bones or bone portions is necessary.

FIGS. 4 through 9 illustrate methods of fixating bone portions according to the present invention, specifically showing the utilization of the implant device 10 to fixate portions of a bone which has suffered a traumatic fracture so as to enable proper and well-aligned healing of the bone.

In FIG. 5 a bone 70 is shown in partial schematic view with a traumatic fracture 72 running through a portion thereof. The portions of the bone which lie on either side of the fracture 72 are denoted 32 and 34. At the outset of the reduction procedure, after an incision has been made in the skin on one side of the bone proximate to the fracture site and has been deepened until the near-side cortex 74 of the bone 70 can be seen and the bone portions 32 and 34 have been manually or otherwise aligned into proper position, an elongated round rectilinear bore 30 having a diameter which is slightly greater than the greatest effective cross-sectional dimension of the head 12 with the arms 20 folded into collapsed position is drilled, utilizing a surgical drill, through the cortex 74 and the bone portions 32 and 34 until the bore penetrates the far-side cortex 76 of the bone 70. Holding the implant device by the tubular guiding member 54, the head 12 with the arms 20 attached thereto in the collapsed position is inserted into the bore 30 beyond the cortex 76 until it presses the soft tissue 78 which is situated beyond the far-side cortex 76.

As illustrated in FIG. 5, the head 12 is then further pushed up into the soft tissue material 78 until the distal ends 25 of the arms 20 have emerged from the bore 30 and are positioned on the far side of the cortex 76. The arms 20 then are deployed from their collapsed position to their extended position in grasping the tubular guiding member with a surgical pliers 80 or a similar suitable instrument and simultaneously pulling downwardly on the free end 38 of the multi-filament thread 36 with a forceps 82 or other appropriate implement, the term "downwardly" being defined as the direction away from the head 12 of the implant device and away from the bone 70 toward the skin surface.

The tension created by pulling on the free end 38 of multi-filament thread 36, and the tension subsequently caused thereby in the individual filaments 46 which extend from the multi-filament thread at its splayed end 44 and which have ends 52 attached to the offset portions 23 of the arms 20, causes the offset portions 23 to be swung in the direction of the head 12 until the upper edges 24 of the arms 20 are snugly seated in the grooves 28 provided in the lateral surface 16 of the head 12, at which point the arms are in their extended positions. The arms 20 are shown in phantom lines in partially extended positions in FIG. 5.

As shown in FIG. 6, subsequent to the deployment of the arms 20 to their extended positions, the multi-filament thread and the tubular guiding member 54 are pulled downwardly until the inner edges 26 of the arms 20 are tightly pressed against the farside cortex 76 of the bone 70. A downward force is then applied to the tubular member 54 until its upper end 56 separates from the lower end 18 of the head 12 and the tubular member 54 thereupon is entirely removed from the bore 30. At this point, if the position and orientation of the implant device with respect to the bone 70, the bone portions 32 and 34, and the fracture 72 are satisfactory, the implant device is secured in position with the multi-filament thread under tension.

As illustrated in FIG. 8, the securing means can comprise a disk 84 which has a transverse dimension greater than the diameter of the bore 30 and which has a hole 86 in the center thereof. The free end 38 of the multi-filament thread 36 is threaded through the hole 86 in the disk 84 and the disk 84 is then pressed firmly against the near-side cortex 74 of the bone 70.

A prong 88 is provided on the underside 90 of the disk 84 about which prong the free end 38 of the thread 36 may be tied so that the disk 84 is securely positioned and the entire implant device 10 is firmly anchored with clamping pressure being applied on the cortices 76 and 74 of the bone 70 by the arms 20 and the securing disk 84, urging the bone portions 32 and 34 toward each other and causing reduction of the fracture 72.

FIG. 9 illustrates the implant device 10 in position and compressing the bone portions 32 and 34 after a substantial period of time has elapsed from the initial implantation of the device. The collapsing tubular mesh 62, which is made of material adapted for losing tensile strength and dissolving in vivo, has already dissolved. As can be seen from FIG. 9, new regenerated bony material 91 is filling up the bore 30 around the multi-filament thread 36 and the fracture 72 has progressed substantially in the healing process. In contrast to the prior art compression means such as bone screws, the bony material is able to fill up almost the entire cavity of the drilled bore 30 even with the bone-fixating implant in place because of the very thin diameter of the multi-filament thread 36 which is the only portion of the implant device that is positioned between the two cortices 74 and 76 of the bone.

In addition to the foregoing, the implant device of the present invention provides for easy removal and repositioning procedures when such removal or repositioning is deemed to be desirable, even after the implant device 10 has been positioned and the securing disk 84 is tightly engaged.

To remove the device 10 after it has been inserted and secured, the free end 38 of the multi-filament thread 36 is cut and the disk 84 removed. The guiding tube 54 is then reinserted into the bore 30 and the multi-filament thread 36 drawn through the interior passageway 60 of the tube 54. The tube 54 is pushed inside the collapsing mesh 62 (not yet dissolved) until the upper end 56 of the tube 54 abuts against the lower end 18 of the head 12. As shown in FIG. 7 in phantom, the head 12 and the arms 20 of the device then are pushed up beyond the far side of the cortex 76 of the bone 70 into the soft tissue material 78 by manipulation of the guiding tube 54 until there is sufficient clearance for the arms 20 to be collapsed from their extended position.

A tissue hook 92 or similar slender instrument (see FIG. 7) with a grasping end 94 is then inserted into the bore 30 until the grasping end 94 firmly engages the collapsing mesh 62. The tissue hook 92 thereupon is pulled downwardly while the guiding tube 43 is simultaneously pushed upwardly, thus creating tension in the collapsing filaments 64 which causes the offset portions 23 of the arms to swing downwardly and effects the collapsing of the arms from their extended positions to their collapsed positions. Alternatively, the collapsing mesh 62 can be pulled downward by grasping and pulling the ends of the pulling filaments 66. Once the arms 20 are in their collapsed positions, the implant device can easily be removed from the bore 30 by further pulling down on the tissue hook 92 or the pulling filaments 66, while maintaining slight retrograde pressure on the guiding tube.

In order to reposition the device after removal, the bore can be modified or another round rectilinear bore can be drilled in a different position and the device can be reinserted in accordance with the procedure previously described.

In FIG. 10 the implant device 10 of the present invention is shown with a generally conical boring cap 96 attached to the upper surface 14 of the head 12. The boring cap 96 is composed of a material dissolvable in vivo. The boring cap 96 is operative for allowing easier passage of the head 12 into the soft material 78 which lies beyond the far-side cortex 76 of the bone 70 through which the implant is inserted. The boring cap 96 has slots 97 through the surface thereof through which the individual filaments 46 are inserted.

In FIG. 11 the implant device 10 is shown provided with a plurality of elongated flexible shielding strips 98 each of which is attached at an end 100 to the upper surface 14 of the head 12 in line with a different one of the grooves 28. Each of the shielding strips 98 extends downwardly from the head 12 and has a lower end 102 which abuts against the crest of the offset portion 23 of a different one of the arms 20.

Each of the shielding strips 98 is positioned so as to protect a different one of the grooves 28 as well as the upper edge 24 of the associated arm 20 from bone or tissue debris that might become lodged in said groove or on said upper edge when the implant device is inserted through the bone portions, thus preventing the snug seating of the upper edges 24 of the arms into the grooves 28 when the arms are deployed from their collapsed positions to their extended positions. As the arms are so deployed, each of the ends 102 of the strips 98 which rests on the offset portion 23 of the associated arm slides upwardly with the arm and out of the way of the groove 28, thus permitting an upper edge 24 of an arm 20 to be seated tightly in the groove 28.

Another novel feature of the present invention is illustrated in FIG. 12, wherein a series of nodes in the form of, for example, balls 104 are secured to the multi-filament thread 36 at spaced intervals. The balls 104 provide surfaces around which the new regenerated bony material 90 can form when the drill-bore 30 is healing and being filled in. Moreover, the balls 104 help anchor the implant device in the bony material 91 and prevent slippage thereof after healing.

When the multi-filament thread 36 is provided with balls 104 as shown in FIG. 12, the securing means comprises a disk 106 provided with a radial slot. A portion of the multi-filament thread which lies between two of the balls 104 is inserted into the radial slot of the securing disk 106 with one of the balls bearing against the surface of the disk and the disk is pressed tightly against the near-side cortex 74 of the bone 70. The disk can be of a variety of thicknesses depending on the degree of bone compression desired.

In another embodiment of the invention, shown in FIG. 13 the arms 20 of the implant device 10 have sharp terminal edges 108 on their distal ends 25. The implant device shown in FIG. 13 is particularly useful in applcations where there is no far-side cortex for the head and arms of the device to rest against, i.e., where the bore is blind. The arms 20 of the implant device 10 shown in FIG. 13 are of such configuration and dimension that a lesser degree of pivotal swinging movement is required before the upper edges 24 of the arms 20 are seated in the grooves 28 in the head, and so that when the arms 20 are fully deployed to the extended position the sharp terminal edges 108 are positioned to bite and grip into the walls of the bore into which the implant will be inserted.

In the implant device shown in FIG. 13, a shaft 110 is attached to the lower end 18 of the head 12, which shaft can be either threaded or have a plurality of annular flanges attached thereto along at least its lower portion. The aperture 42 through the head 12 through which the multi-filament thread 36 extends is off-centered in the head 12 and is positioned so that the multi-filament thread 36 emerges from the head adjacent to the shaft 110. The multi-filament thread 36 then extends alongside the shaft 110 towards the lower end 40 of the implant device.

FIG. 13A illustrates a bowed push-on nut 112 which can be utilized as the securing means when the implant device is provided with a shaft such as the shaft 110 having a plurality of annular flanges thereon. After the implant is inserted into the bore in the bone portions, with a portion of the end of the shaft 110 still protruding from the open end of the bone bore, the nut 112 is pressed forcibly down on the shaft 110 until the nut 112 abuts against the cortex of the bone through which the bore hole was drilled.

In FIG. 14 the implant device 10 having arms 20 with sharp terminal edges 108 is illustrated in position fusing the first metatarsal bone 114 of a human foot to the medial cuneiform bone 116 thereof. The base of the first metatarsal has been resected including the articular cartilage thereof and the articular cartilage of the medial cuneiform distal surface has also been removed to allow maximum bone-to-bone contact to facilitate fusion. This surgical procedure is utilized to correct a deviated first metatarsal where removal of a wedge of bone from the first metatarsal base and subsequent co-adaptation of the bone portions will cause the first metatarsal to deviate to the proper angle.

Because of the position of the implant device in FIG. 14, there is no cortex of the cuneiform on which the head 12 and the arms 20 of the device can rest, but, instead, the sharp edges 108 of the arms grip and bite into the medullar material inside the cuneiform surrounding the bore 109. The device shown in FIG. 14 is provided with a threaded shaft 110 and is secured by means of, for example, a push-on nut 112.

In FIG. 15 an implant device 10 is shown in position fixating the first metatarsal bone 119 of a human foot to the second metatarsal bone 120 thereof and decreasing the angle between the two bones. The multi-filament thread 36, in this instance, traverses the interspace 122 between the two metatarsals. The fixation of the metatarsals illustrated in FIG. 15 would be highly useful in surgery aimed at reducing deviation of the first metatarsal in a bunion deformity.

Another important application of the implant device of the present invention is shown in FIG. 16. A plurality of small implant devices and a large implant device are shown in fully deployed and secured condition attaching a compression plate apparatus 130 to a human femur 132, reducing a fracture 134 of the femoral neck 136. The compression plate apparatus 130 has a plate portion 138 pressed against the lateral cortex 140 of the femur and secured by implant devices 126 which extend through the femur with the head 12 and arms 20 of each device pressing against the medial cortex 146 of the femur.

The apparatus 130 further has a tubular angulated portion 148 affixed to the plate portion 138 and extending into the femoral neck 136 at an obtuse angle from the lateral cortex 140 and crossing the fracture line. The femur is properly reamed out prior to the insertion of the tubular portion 148 of the apparatus 130 therein.

The large implant device 128 has a threaded shaft 150 attached to its head 12, which shaft extends through the tubular portion 148, while the arms 20 of the implant device 128 terminate in sharp edges 108 which are anchored in the medulla of the medial side of the fracture 134. More specifically, the sharp edges 108 of the arms 20 bite into and grip the medullary material which surrounds the bore 152 through which the large implant device 128 is inserted. A fixating tube can be inserted into the bore 152 and around the shaft 150 to stabilize and fixate the implant device and prevent movement of the head of the implant device within the bore. The end of the shaft 150 of the implant device 128 is then tightly secured against the tubular portion 148 of the compression apparatus 130 by a washer 156 and a nut 158. In the embodiments of the fixating device shown in FIG. 16, the multi-filament deploying threads are not shown inasmuch as the devices shown in that figure are already in fully deployed condition, any excess thread has already been cut away and the protruding ends of the devices have been secured.

The small implant devices 126, shown in FIG. 16, are similarly provided with threaded shafts 160 which are secured against the plate portion 138 of the apparatus 130 by nuts 162.

The entire arrangement of implant devices and compression apparatus depicted in FIG. 16 operates to reduce the fracture 134 of the femoral neck 136 and fixates the neck portions 164, 166 which lie on either side of the fracture in tight alignment even under the conditions of great stress such as are normally applied to a human femur during walking and more strenuous activities.

The large implant device 128 which is inserted through the tubular portion 148 of the compression plate apparatus and through the bore 152 into the femoral neck 136 is greatly superior to prior art devices for the impaction and fixation of the portions 164, 166 of the femoral neck 136 which lie on either side of the fracture 134. When the device 128 has been positioned with the arms 20 deployed and gripping into the medually material surrounding the bore 152, the lower end of the shaft 150 can be pulled away from the femur until the bone portions on either side of the fracture have been impacted, a step necessary to promote rapid and proper healing.

After the washer 156 and the nut 158 have been fastened to the end of the shaft 150 and secured against the compression apparatus 130, any excessive protruding portion of the shaft 150 can be easily cut or clipped off and discarded, because the shaft 150 is of relatively small diameter in comparison with prior art bone screws, bolts, and so on, and is constructed of a somewhat flexible material.

This procedure for impacting the femoral neck fragments by pulling the portion of the femoral neck 164 which lies on the far side of the fracture towards the portion 166 which is on the near side of the fracture is in marked contrast to the prior art procedure which utilizes devices of fixed lengths and necessiates the hammering of the femoral shaft into the femoral neck to achieve impaction and to measure the length of the resultant bore as has been described previously. This prior art procedure involves a number of hazards, including the possibility of serious damage to the hip joint and the tissue surrounding the femoral head. In addition, the compressive force provided by the present device, with the extended arms 20 biting into the medulla of the femur and the washer and nut tightly securing the lower end of the device against the cortex, is greater than that which has been achieved with any previous device that was thin or flexible enough to permit the cutting off of any excessive length.

The implant devices of the present invention can be constructed of a variety of surgically approved metallic alloys including, for example, titanium alloys having superior pitting resistance and anti-corrosion properties which make them highly compatible with body tissue. In addition, low carbon annealed stainless steel and cobalt-based alloys can be utilized.

The multi-filament thread of the implant device can be constructed of fine stainless steel wires of high tensile strength or of surgical silk, surgical-grade nylon, or surgical-grade polypropylene. Pins or wires which would be used in some embodiments of the invention in conjunction with the multi-filament thread could be conventional Steinman pins and Kirschner wires which are available in a variety of stainless steel and cobalt-based alloys.

The collapsing mesh of the implant device is composed of a bodydissolvable suture-type material such as polyglactin 910 (VICRYL) or polyglycolic acid (DEXON), both manufactured by Ethicon. These materials will lose tensile strength and subsequently dissolve or disintegrate when the implant is in position inside the body.

For certain surgical applications, the head and arms of the implant could be made of a surgical-grade plastic which is ductile enough to allow for fashioning of a living hinge between each arm and the head.

The various embodiments of the implant device of the present invention provide numerous advantages over the currently used orthopedic surgical implants, including ease of insertion and positioning, rapid healing of the transcortical bore even when the implant is in position, excellent compression to accelerate fusion or provide substantial immobility of bones for corrective purpose, and less likelihood of bone cracking around the implant site.

While the invention has been illustrated and described as a surgical implant device operative for fixating adjacent bone or bone portions, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various mechanisms without omitting features that, from the standpoint of the prior art, fairly constitute essential characteristics of the generic or specific aspects of this invention, and therefore, such adaptations should and are intended to be comprehended within the meaning and range of equivalents of the following claims.

What is claimed as new and designed to be protected by Letters Patent is set forth in the appended claims.

1. A surgical implant device for fixating bones in which a round rectilinear bore has been drilled, said device having an upper end region and a lower end region and comprising:
(a) a head positioned at the upper end region of the device;
(b) a plurality of arms, each having a proximal and a distal end;
(c) means for hingeably connecting the proximal ends of the arms to the head so that said arms may be deployed by radial upward swinging movement from a downwardly extending retracted position, wherein said arms are spaced a predetermined angular distance from the head and wherein the greatest effective transverse dimension of the head and of the connected arms is less than the diameter of the bore drilled in the bone so that the head with said arms in the retracted position may be inserted into said bore, to an extended position wherein the arms are spaced from the head at an angular distance which is less than said predetermined distance and wherein the greatest effective transverse dimension of said head and connected arms is greater than the diameter of said bore;
(d) shaft means for guiding the insertion of the head and arms of the implant device into the bore, said arms being at all times positioned exteriorly of said shaft means;
(e) manually operable pull-type actuating means connected to the arms for deploying the arms from the retracted position to the extended position after said head and connected arms have been inserted into the bore; and
(f) manually effectuatable means for firmly securing the lower end region of said implant device which is opposite the head against portions of the bone surrounding the bore and exerting downward force on the head and arms subsequent to the insertion of the head and connected arms into the bore and their deployment to the extended position.

2. An implant device according to claim 1 wherein there is additionally provided pull-type means for collapsing the arms from the extended position to the retracted position, after the insertion of the head and arms into the bore, to permit the removal of the head and arms from the bore.

3. An implant device according to claim 2 wherein:
(a) the head has an elongated aperture extending therethrough substantially in the direction of the opposite end region of the device; and
(b) the pull-type actuating means for deploying the arms comprises an elongated thread having a free end near the lower end region of the device and extending from said free end through the aperture in the head and having a splayed end at which the thread is divided into a plurality of individual filaments, each of which extends from the head aperture to an outer thread end operatively attached to a portion of a different one of the arms at a point spaced from the proximal end so that tension in the thread caused by pulling on the free end thereof actuates the deployment of the arms from the retracted position to the extended position.

4. An implant device according to claim 3 wherein the guiding shaft means comprises an elongated hollow tubular member having:
(a) an upper end adjacent to the head and a lower end adjacent to the lower end region of the implant device;
(b) an interior central passageway through which the thread is threaded, entering the passageway at the upper end of the tubular member adjacent to the head and emerging from the passageway at the lower end of the tubular member with the free end of the thread extending beyond said lower end.

5. An implant device according to claim 4 wherein said tubular member is detachably coupled at its upper end to the head.

6. An implant device according to claim 4 wherein the collapsing means comprises:
   (a) a cylindrical member which girdles a portion of the tubular guiding member and is slideably mounted thereon; and
   (b) a plurality of collapsing filaments, the number of said filaments being equal to the number of arms, and each of said collapsing filaments extending from the cylindrical member and having an outer end attached to a portion of a different one of the arms at a point spaced from the proximal end so that when the cylindrical member is displaced along the tubular member in a direction away from the head towards the lower end of said tubular member, the collapsing filaments cause the arms to collapse from the extended position to the retracted position.

7. An implant device according to claim 6 wherein said girdling member comprises a cylindrical mesh composed of a material that will lose tensile strength and substantially dissolve in vivo within 20 days of the implantation of the device.

8. An implant device according to claim 3 wherein said securing means comprises a button having thereon means for grasping a portion of the thread in the vicinity of its free end so as to cause tension in the thread, and adapted when positioned for exerting a compressive force on the portions of the bone surrounding the bore.

9. An implant device according to claim 8 wherein said grasping means comprises a prong extending from a surface of the button, said prong being spaced away from the bone portions surrounding the bore when the button is in position against said bone portions.

10. An implant device according to claim 3 wherein:
    (a) the thread has a plurality of spread nodes thereon from the point where the thread emerges from the aperture in the head to a point near the free end of the thread; and
    (b) the securing means comprises a disk having a radial slot extending from the edge thereof, said disk having a diameter greater than the diameter of the bore drilled through the bone and being suitable for placement over the opening of the bore in the bone, and bearing against a node on the thread with a portion of the thread that lies between two nodes inserted into the slot, thus preventing slippage of the thread and anchoring the implant device in position.

11. An implant device according to claim 3, wherein the head has a boring cap affixed thereto which has a generally conical configuration and which has slots provided therein through which the individual filaments which extend from the splayed end of the thread to the arms are inserted.

12. An implant device according to claim 2 wherein:
    (a) the guiding shaft means comprises a threaded shaft attached to the head and extending towards the lower end region of the device with a lower end that protrudes beyond the opening of the bore in the bone when the device is inserted into the bore;
    (b) the aperture through the head is non-central and is adjacent to the area of juxtaposition between the shaft and the head;
    (c) the thread extends from its splayed end through the aperture and along the outside of the shaft toward the lower end thereof;
    (d) the securing means comprises a bolt-fastening arrangement, said bolt-fastening arrangement being fastened to the lower end of the shaft after the implant device has been inserted into the hole and the arms have been deployed.

13. An implant device according to claim 3 wherein:
    (a) the guiding shaft means comprises a shaft with a plurality of annular flanges attached thereto and spaced along at least a portion of its length, said shaft being attached to the head and extending toward the lower region of the device with a lower end that protrudes beyond the opening of the bore in the bone when the device is inserted into the bore;
    (b) the aperture through the head is adjacent to the area of juxtaposition between the shaft and the head;
    (c) the thread extends from its free end along the outside of the shaft and through the aperture; and
    (d) the securing means comprises a push-on nut.

14. An implant device according to claim 1 wherein there are additionally provided a plurality of axial grooves in a lateral surface of the head, the number of said grooves being equal to the number of arms, said grooves being situated so that when the arms are deployed from the retracted position to the extended position, an upper edge of each arm is freely received by a different one of the grooves in the head.

15. An implant device according to claim 14 wherein there are additionally provided flexible elongated shielding strips, the number of said strips being equal to the number of arms, and each of said strips having one end attached to the head in line with one of the grooves and extending downwardly from the head to abut against one of the arms, said strips being of sufficient length and width to shield the grooves and arms from debris when the head and arms are inserted through the bore drilled through the bone.

16. An implant device according to claim 1 wherein each arm terminates in an edge adapted for biting and anchoring into the medulla of the bone surrounding the bore into which the implant device is inserted, thereby anchoring the head of the implant device in the bone and preventing slippage thereof.

17. A method for fixating at least one portion of at least one bone utilizing a bone fixating surgical implant device operative for fixating bones in which a round, rectilinear bore has been drilled, said device having an upper end region and a lower end region and comprising a head positioned at the upper end region of the device; a plurality of arms, each having a proximal end and a distal end; means for hingeably connecting the proximal ends of the arms to the head so that said arms may be deployed by radial upward swinging movement from a downwardly extending retracted position, wherein said arms are spaced a predetermined angular distance from the head and wherein the greatest effective transverse dimension of the head and of the connected arms is less than the diameter of the bore drilled in the bone so that the head with said arms in the retracted position may be inserted into said bore, to an extended position wherein the arms are spaced from the head at an angular distance which is less than said predetermined distance and wherein the greatest effective transverse dimension of said head and connected arms is greater than the diameter of said bore; shaft means for guiding the insertion of the head and arms of the implant device into the bore, said arms being at all times positioned exteriorly of said shaft means; manually operable pull-type actuating means connected to the arms for deploying the arms from the retracted position to the extended position after said head and connected arms have been inserted into the bore; and manually effectuatable means for firmly securing the lower end region of said implant device which is opposite the head against portions of the bone surrounding the bore and exerting downward force on the head and arms subsequent to the insertion of the head and connected arms into the bore and their deployment to the extended position, said method comprising the steps of:

(a) making an incision in the skin proximate to the bone portions to be fixated;

(b) deepening the incision until a near-side cortex of a first bone portion to be fixated can be seen;

(c) drilling a round rectilinear bore through the near-side cortex and through the first bone portion and all other bone portions which are to be fixated, the diameter of said bore being slightly greater than the greatest effective transverse dimension of the implant device with the arms in retracted position;

(d) inserting the head and arms of the implant device, said arms being in retracted position, into the bore in the bone portions until the distal ends of the arms have emerged from the bore and are positioned on the far side of the cortices of all bone portions which are to be fixated and a portion of the lower end region of the device still protrudes from the opening of the bore in the near-side cortex of the first bone portion;

(e) deploying the arms of the implant device from the retracted position to the extended position;

(f) pulling the protruding portions of the lower end region of the device in a direction away from the head until the arms are firmly anchored on the farside cortex of a bone portion; and (g) utilizing the securing means to tightly fasten the protruding portion of the lower end region of the device to an area of the near-side cortex of the first bone portion surrounding the opening of the bore.

18. A method of removing a bone fixating surgical implant device for fixating bones in which a round rectilinear bore has been drilled, said device having an upper end region and a lower end region and comprising a head positioned at the upper end region of the device; a plurality of arms, each having a proximal end and a distal end; means for hingeably conneting the proximal ends of the arms to the head so that said arms may be deployed by radial upward swinging movement from a downwardly extending retracted position, wherein said arms are spaced a predetermined angular distance from the head and wherein the greatest effective transverse dimension of the head and of the connected arms is less than the diameter of the bore drilled in the bone so that the head with said arms in the retracted position may be inserted into said bore, to an extended position wherein the arms are spaced from the head at an angular distance which is less than said predetermined distance and wherein the greatest effective transverse dimension of said head and connected arms is greater than the diameter of said bore; shaft means for guiding the insertion of the head and arms of the implant device into the bore, said arms being at all times positioned exteriorly of said shaft means; manually operable pull-type actuating means connected to the arms for deploying the arms from the retracted position to the extended position after said head and connected arms have been inserted into the bore; manually effectuatable means for firmly securing the lower end region of said implant device which is opposite the head against portions of the bone surrounding the bore and exerting downward force on the head and arms subsequent to the insertion of the head and connected arms into the bore and their deployment to the extended position; and means for collapsing the arms from the extended position to the retracted position after the insertion of the head and arms into the bore, including a cyclindrical member which girdles a portion of the guiding shaft means and is slideably mounted thereon and a plurality of collapsing filaments, the number of said filaments being equal to the number of arms, and each of said collapsing filaments extending from the cylindrical member and having an outer end attached to a portion of a different one of the arms at a point spaced from the proximal end so that when the cyclindrical member is displaced along the guiding shaft means in a direction away from the head towards the lower end of said tubular member, the collapsing filaments cause the arms to collapse from the extended position to the retracted position, said removal being performed after the device has been inserted into the bore, the arms deployed to their extended position and pressing against a far-side cortex of a bone portion, and the securing means affixed, said method comprising the steps of:

(a) removing the securing means from the end of the implant device;

(b) pushing the guiding means into the bore so that the head and arms are raised from the position in which the arms were firmly anchored on the farside cortex of the bone portion until there is clearance for the arms to be collapsed from their extended position to their retracted position;

(c) pulling the cylindrical girdling member along the guiding shaft away from the head until the arms are collapsed from their extended position to their retracted position; and (d) pulling the cylindrical girdling member until the head and arms of the implant device are removed from the bore.

* * * * *